United States Patent [19]

Verkade

[11] Patent Number: 4,885,376

[45] Date of Patent: Dec. 5, 1989

[54] NEW TYPES OF ORGANOMETALLIC REAGENTS AND CATALYSTS FOR ASYMMETRIC SYNTHESIS

[75] Inventor: John G. Verkade, Ames, Iowa

[73] Assignee: Iowa State University Research Foundation, Inc., Ames, Iowa

[21] Appl. No.: 107,347

[22] Filed: Oct. 13, 1987

[51] Int. Cl.$^4$ ...................... C01G 55/00; C01G 23/00; C01G 53/00

[52] U.S. Cl. .......................................... 556/18; 556/19; 556/30; 556/54; 556/56; 556/76; 556/136; 556/137; 556/146

[58] Field of Search ........................ 556/19, 54, 56, 76, 556/136, 137, 146, 18, 30

[56] References Cited

U.S. PATENT DOCUMENTS

| | | | |
|---|---|---|---|
| 3,345,392 | 10/1987 | Grayson et al. | 260/438.1 |
| 3,798,241 | 3/1974 | Kagan et al. | 556/18 |
| 3,799,961 | 3/1974 | Sergeevich et al. | 260/429 R |
| 3,891,684 | 6/1975 | Jung | 260/429 R |
| 4,180,386 | 12/1979 | McCormack et al. | 556/21 |
| 4,497,737 | 2/1985 | Sargeson et al. | 556/137 |
| 4,650,609 | 3/1987 | Brittelli | 556/18 |

FOREIGN PATENT DOCUMENTS

| | | |
|---|---|---|
| 164970 | 12/1985 | European Pat. Off. . |
| 0278684 | 8/1988 | European Pat. Off. ............. 556/56 |
| 57-195163 | 11/1982 | Japan . |
| 950732 | 8/1982 | U.S.S.R. . |
| 2123422 | 7/1982 | United Kingdom . |

Primary Examiner—H. M. S. Sneed
Assistant Examiner—J. Saba
Attorney, Agent, or Firm—Zarley, McKee, Thomte, Voorhees & Sease

[57] ABSTRACT

New chiral catalysts for asymmetric synthesis reactions. The catalysts induce chirality in desired fashion in product molecules. The catalysts are rigid quadruped or triped ligands which provide a rigid asymmetric enantio-face at the active catalyst cite, thus inducing preparation of enantiomer molecules.

9 Claims, No Drawings

NEW TYPES OF ORGANOMETALLIC REAGENTS AND CATALYSTS FOR ASYMMETRIC SYNTHESIS

BACKGROUND OF THE DISCLOSURE

This invention relates to asymmetric synthesis. Asymmetric synthesis is of general interest, often in the pharmaceutical industry, since frequently only one optically active isomer (enantiomer) is therapeutically active. Thus, in many processes, some of which include hydrogenation, olefin isomerization, hydrocarbonylation, hydrocyanation, oxidation, cyclooligomerization and hydroformylation, it is desirable to induce formation of one particular enantiomer over its mirror image. Currently, asymmetric induction can be carried out with organometallic catalysts having optically active ligands such as PR'R"R''' in (PPh$_3$)$_2$Rh(PR'R"R''')Cl. Seldom is the asymmetric induction ever near 100% effective, however, in part because the substrate molecule can take more than one directional approach in attacking the metallic center of the catalyst molecule.

There is therefore a real and continuing need to provide catalysts which will allow more efficient asymmetric induction to yield the desired enantiomer. This invention has as its primary objective the fulfillment of this need.

Another objective of the present invention is to provide chiral catalysts of quadruped ligands which are highly effective in induction of chirality in substrate molecules.

Yet another objective of the present invention is to prepare chiral catalysts of triped ligands which are highly effective in induction of chirality into substrate molecules.

A further objective of the present invention is to provide a method of inducing organic synthesis reactions to produce high yields of desired chiral molecules by employing organometallic catalysts containing chiral ligands which establish a single rigid enantio-face near the catalyst site, thus preventing multiple approaches of the substrate molecule to the catalytic complex, and thereby inducing chirality.

The method and manner of accomplishing each of the above objectives will become apparent from the detailed description of the invention which follows.

SUMMARY OF THE INVENTION

This invention relates to catalysts for asymmetric synthesis which induce chirality into the synthesized molecules at good yield levels. The catalyst molecules are novel triped or quadruped ligands which when bound to a metal atom are rigid, and therefore present a rigid enantio-face to the substrate molecule that attacks the active site of the catalytic complex. As a result, chirality is induced. The invention, besides relating to the novel catalysts, also relates to a method of inducing asymmetric synthesis.

DETAILED DESCRIPTION OF THE INVENTION

The catalysts of this invention contain either a quadruped ligand or a triped ligand. The quadruped catalysts have the general structural formula:

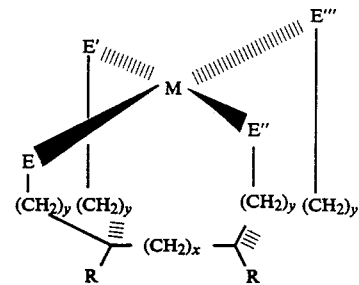

wherein M is a transition metal of Group 3–12 of the periodic chart, E, E', E", and E''' are selected from the group consisting of organo electron donor moieties of phosphorus, (e.g. phosphines or phosphinites) nitrogen (amines and amides), arsenic (arsines), oxygen and sulfur, wherein y is from about 1 to about 3, x is from 0 to about 4, R and R' are selected from the group consisting of hydrogen, C$_1$ to C$_{10}$ alkyl, phenyl, and ring systems wherein R and R' are (CH$_2$)$_z$ and z is from 1 to about 4.

As used herein, the reference to the "groups" of the periodic table refers to the modern grouping terminology, that is beginning with group 1, numbering sequentially from left to right across the entire table. The preferred metals are transition metals of palladium, rhodium, platinum, nickel, titanium, zirconium and hafnium.

E, E', E" and E''' each refer to the corner atoms or groups of the quadruped ligand. Each of E, E', E" and E''' must be selected so that the catalyst molecule itself is chiral. The only important criterion is that the molecule itself be chiral and thus each of E, E', E" and E''' need not be different. For example, one corner atom or group chemically different from three identical other corner moieties imparts chirality to the ligand as well as the catalyst. Likewise, having E and E''' the same and E" and E' the same but different from E and E''' also imparts chirality. Combinations of moieties for each of the four corners (E, E', E" and E''') which impart chirality are well within the skill of the art and need not be recited herein. Each of these corner atoms or groups is an electron donor moiety to the metal M. The donor atom of the electron donor group may be a group 15 or 16 atom, commonly phosphorus, nitrogen, arsenic, oxygen, or sulfur. Preferably it is phosphorus, nitrogen or oxygen. The remaining bonds required for the electron donor atom (but not specifically depicted) may be to any group such as lower alkyl (C$_1$ to C$_8$) groups, hydroxy groups, amines or the like, this not being critical.

The triped ligand containing chiral catalysts may be represented by the structural formula:

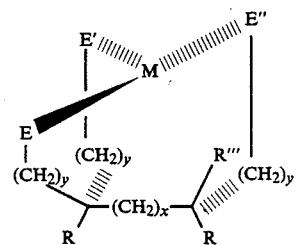

The central metal atom M, the corner atoms E, E'E", R, R', x and y may be as hereinbefore described with regard to the quadruped ligands. R'" may be H or a lower alkyl ($C_1$–$C_8$) group, or a phenyl (or substituted phenyl) group. In a triped ligand, chirality is also present when E=E'=E".

By use of the above described catalysts in conventional organic synthesis reactions, it is possible to produce in yields exceeding 90% products of a preferred optical isomer. It is believed that this occurs because the catalysts hereinbefore described have rigid cage-like structures, and thus provide a rigid enantio-face at the active metallic catalyst site. Thus, the substrate molecule which approaches the catalytic complex can only approach in a single path or, in other words, is stereo directed in a region above the MEE'E"E'" plane in the case of the quadruped catalyst, and in the same region but somewhat more toward the vacant fourth corner in the triped catalyst system. It should be noted that there is insufficient space beneath the M atom for a substrate molecule of any reasonable size (i.e. consisting of more than two atoms). The above process induces the formation of one particular enantiomer to the exclusion of its mirror image. While not wishing to be bound by any theory, it is believed that this results from the stabilization of uncommon coordination geometries of the transition metal (e.g. Ni(O), Ag+, Co+) within the unusual quadrupedal tetradentate or tripedal tridentate ligand. Put another way, the substrate molecule must approach the active cite of the catalyst in a single directionally oriented manner toward the enantio-face in order to reach the active chiral site, and this provides inducement or encouragement for formation of chiral product molecules from the substrate.

The reactions which may be catalyzed using the catalyst of this invention are many, depending upon the metal employed and the corner electron donor atoms within the ligands. Generally speaking, those compounds falling within the definitions previously described may be successfully used for catalyzing hydrogenation, olefin isomerization, hydrocarbonylation, hydrocyanation, oxidation, cyclooligomerization and hydroformylation.

The catalyst ligands may be synthesized by well-known techniques, and the synthesis of the catalyst itself does not form part of this invention. An example of a synthesis for a quadruped ligand starting from a literature compound is shown below.

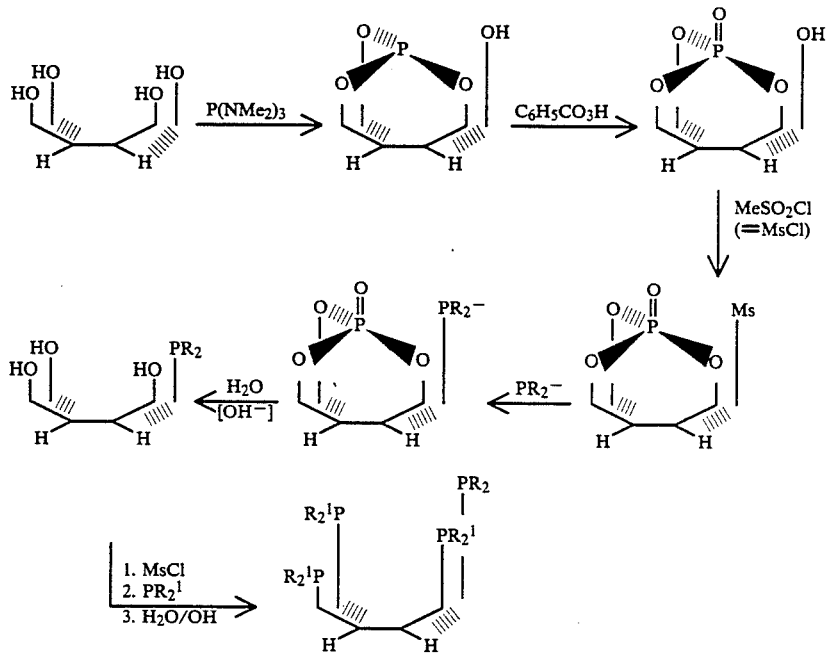

For purposes of describing the theory of this invention, the following general structures are presented in order to understand how the reactive action site of the catalyst is presented to the substrate molecule.

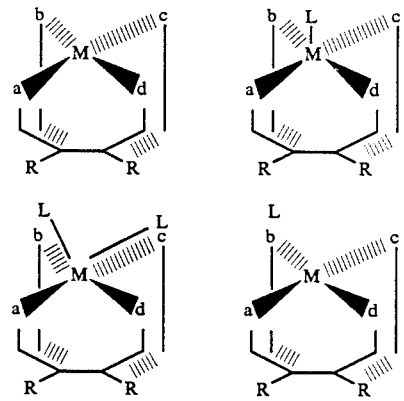

Two dominant features of the ligands discussed in the previous section are the structural rigidity they impose on a chelated metal and the restrictions they place on its coordination sphere. The structural rigidity of the pairs of six- and seven-membered chelate rings depicted in A is apparent from space filling models, whether M lies in the plane of the donor atoms a-d or slightly above it. These models also require that any additional ligands the metal may wish to ligate must lie directly above the a-d plane as in five-coordinate B, and they must deploy in a "vee" configuration in the isomeric/rotameric sixcoordinated structures C and D, owing to the lack of space within the cage for even a diatomic axial ligand.

The apparently snugly chelated structures A-D imply that the tetradentate (quadruped) ligands are well suited to stabilizing rectangular planar, rectangular pyramidal, and trigonal prismatic metal coordination geometries. Two of these geometries represent strained higher-energy stereochemistries for some metals (e.g., M=Ni(O), Ag(I), Zn(II) in A, and M=Fe(O), Co(I), Ni(II) in B) which will enhance their catalytic activity. The two remaining geometries (C, D) represent at least unusual stereochemical possibilities for other metals such as Cr(O), Mn(I), Fe(II) and Co(III). Their higher energies may lead to dissociation of a ligand lying above the Mabcd plane which in turn leads to coordinative unsaturation of the metal, a condition well known to be associated with catalytic activity.

The following examples are offered to illustrate the formation of the precursors for the reactive catalysts of this invention, for preparation of the catalysts of this invention, and to illustrate reactions which may be asymmetrically catalyzed.

EXAMPLE 1

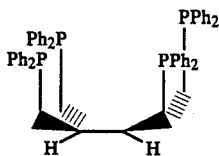

Separate solutions of cis-$(C_6H_5CN)_2PdCl_2$ (0.219/g, 0.57 mmol) and 1 (0.235 g, 0.29 mmol) in 20 mL benzene were prepared. To inhibit formation of polymeric species the solutions were added simultaneously over 1 h to 50 mL benzene, then stirred overnight. The product precipitated from solution as a pale yellow powder which was filtered, washed with ether and dried in vacuo. yield 0.575 g (86% based on $(C_6H_5CN)_2PdCl_2$).

EXAMPLE 2

[Pd1][BF$_4$]$_2$ 2 (0.575 g, 0.49 mmol) and 1 (0.403 g, 0.49 mmol) were heated to 85° C. in 100 mL of DMSO for 5 d under an inert atmosphere to prevent oxidation of the ligand. Half of the DMSO was removed at reduced pressure and CHCl$_3$ added to give a ca. 50/50 solvent mixture. AgBF$_4$ (0.191 g, 0.98 mmol) was added and the precipitated AgCl separated by filtration. Removal of solvent from the filtrate yielded the pale yellow crude product which was purified by recrystallization from acetonitrile. Yield 0.358 g (66% based on 2).

EXAMPLE 3

[Ag1][AsF$_6$]

AgAsF$_6$ (0.131 g, 0.44 mmol) in 20 mL ethanol and 1 (0.362 g, 0.44 mmol) in 20 mL benzene were added simultaneously over 1 h to 50 mL ethanol with vigorous stirring. The reaction was complete within 2 h, and the precipitated white product filtered and washed with ether. The crude material can be recrystallized from acetone or acetonitrile to give fine white needles. Yield 0.432 g (88% based on AgAsF$_6$).

The following table illustrates polycyclic metal complexes which can be analogously prepared in accordance with the present invention and which can be used to catalyze the reactions referred to in the table to provide in high yields chiral molecules.

TABLE I

Polycyclic metal complexes for comparison with catalytic $(M(P-P)_2^+$ or $MP_4^X$ systems

| Metal in polyped structure[a] | Known catalytic compound[b] | Catalytic reaction |
|---|---|---|
| Pd | Pd(Ph$_2$PCH$_2$CH$_2$Ph$_2$)$_2$ | catalyzes alkylation of allylacetates by various nucleophiles |
|  | Pd(PPh$_3$)$_4$ |  |
|  | Pd(PPh$_3$)$_4$ | O—allyl S—alkyl dithiocarbonates produce alkyl allyl sulfides with net retention |
| Rh+ | Rh(PPh$_3$)$_4^+$ | hydrocarbon oxidation |
| Rh+ | Rh(PPh$_3$)$_4^+$ | hydrocarbon oxidation |
| Pd | Pd(PPh$_3$)$_4$ | reactions |
| Ni | Ni(PPh$_3$)$_4$ | cyclooligomerization of butadiene |
|  | Ni(DIOP)$_2$ | asymmetric HCN addition to norbornenes |
| Rh+ | Rh(DIOP)$_2^+$ | asymmetric hydrosilylation of prochiral ketones and hydroesterfication of prochiral olefins |
|  | Ni[P(OPh)$_3$]$_4$ | HCN addition to alkynes |

[a]The metals in this column occur at position M in quadruped structures of the general type given on page 3 or in the triped structure of the general type given on page 5.
[b]In this column are complexes of less constrained, lower energy structures, which are known to catalyze the indicated reactions.

It therefore can be seen that the invention accomplishes at least all of its stated objectives.

What is claimed is:

1. Chiral catalysts having quadriped ligands for induction of chirality in reaction product molecules, said catalysts having the formula:

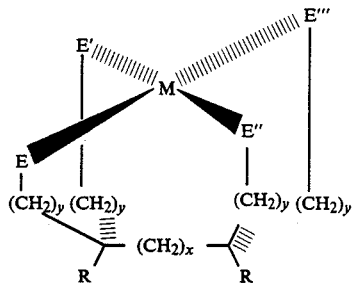

wherein M is a transition metal selected from the group consisting of palladium, rhodium, platinum, nickel, titanium, zirconium and hafnium, E, E', E", and E"' corners are selected from the group consisting of organo electron donor moieties of phosphorus, nitrogen, arsenic, oxygen, sulfur, wherein y is from about 1 to about 3, x is from 0 to about 4, R and R' are selected from the group consisting of hydrogen, C$_1$ to C$_{10}$ alkyl, phenyl, and ring systems wherein R and R' are (CH$_2$)$_z$ and z is from 1 to 4.

2. The catalysts of claim 1 wherein E, E' and E" are the same and all different from E"'.

3. The catalysts of claim 1 wherein E and E"' are the same and E' and E" are different from each other and from E and E"'.

4. The catalysts of claim 1 wherein each of E, E', E" and E'" are different.

5. Chiral catalysts having triped ligands for induction of asymmetry into reacton product molecules yielded from reactions catalyzed by said catalysts, said catalysts having the formula:

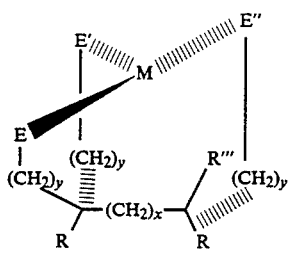

wherein M is a transition metal selected from the group consisting of palladium, rhodium, platinum, nickel, titanium, zirconium and hafnium, E, E', and E" are selected from the group consisting of electron donor moieties of phosphorus, nitrogen, arsenic, oxygen, sulfur, and R and R' are selected from the group consisting of hydrogen, $C_1$ to $C_{10}$ alkyl, phenyl and ring systems wherein R and R' are $(CH_2)_z$ and z is from 1 to 4, and R'" is a hydrogen, aryl or $C_1$ to $C_{10}$ alkyl.

6. The catalyst of claim 5 wherein each of $E_1$, E' and E" are all the same.

7. The catalyst of claim 5 wherein each of E and E' are the same and both different from E".

8. The catalyst of claim 5 wherein E, E' and E" are all different.

9. The catalyst of claim 1 wherein E, E', E" and E'" are diphenylphosphine, where "M" is palladium, "Y" is 1, "X" is 0, and R and R' are hydrogen.

* * * * *